(12) United States Patent
Lizardi

(10) Patent No.: US 6,527,795 B1
(45) Date of Patent: Mar. 4, 2003

(54) KNOTLESS SUTURE ANCHOR SYSTEM AND METHOD OF USE

(75) Inventor: Jose E. Lizardi, Franklin, MA (US)

(73) Assignee: Ethicon, Inc., Somerville, NJ (US)

( * ) Notice: Subject to any disclaimer, the term of this patent is extended or adjusted under 35 U.S.C. 154(b) by 118 days.

(21) Appl. No.: 09/691,498

(22) Filed: Oct. 18, 2000

(51) Int. Cl.$^7$ .............................................. A61B 17/04
(52) U.S. Cl. ..................................................... 606/232
(58) Field of Search ............................ 606/72–75, 225, 606/232

(56) References Cited

U.S. PATENT DOCUMENTS

| | | |
|---|---|---|
| 65,499 A | 6/1867 | Miller |
| 1,082,540 A | 12/1913 | MacColl et al. |
| 1,293,660 A * | 2/1919 | Armstrong .................. 223/102 |
| 4,007,743 A | 2/1977 | Blake |
| 4,378,019 A | 3/1983 | Yamada |
| 4,532,926 A | 8/1985 | O'Holla |
| 4,537,185 A | 8/1985 | Stednitz |
| 4,632,101 A | 12/1986 | Freedland |
| 4,721,103 A | 1/1988 | Freedland |
| 4,870,957 A | 10/1989 | Goble et al. |
| 4,898,156 A | 2/1990 | Gatturna et al. |
| 4,946,468 A | 8/1990 | Li |
| 4,976,715 A | 12/1990 | Bays et al. |
| 5,002,550 A | 3/1991 | Li |
| 5,013,316 A | 5/1991 | Goble et al. |
| 5,021,059 A | 6/1991 | Kensey et al. |
| 5,037,422 A | 8/1991 | Hayhurst et al. |
| 5,074,874 A | 12/1991 | Yoon et al. |
| 5,084,050 A | 1/1992 | Draenert |
| 5,100,417 A | 3/1992 | Cerier et al. |
| 5,102,421 A | 4/1992 | Anspach, Jr. |
| 5,123,913 A | 6/1992 | Wilk et al. |
| 5,129,906 A | 7/1992 | Ross et al. |
| 5,129,912 A | 7/1992 | Noda et al. |
| 5,141,520 A | 8/1992 | Goble et al. |
| 5,152,765 A | 10/1992 | Ross et al. |
| 5,152,769 A | 10/1992 | Baber |
| 5,178,629 A | 1/1993 | Kammerer |
| 5,192,303 A | 3/1993 | Gatturna et al. |
| 5,207,679 A | 5/1993 | Li |
| 5,224,946 A | 7/1993 | Hayhurst et al. |
| 5,226,535 A | 7/1993 | Rosdhy et al. |
| 5,236,431 A | 8/1993 | Gogolewski et al. |
| 5,236,445 A | 8/1993 | Hayhurst et al. |
| 5,258,016 A | 11/1993 | DiPoto et al. |
| 5,259,846 A | 11/1993 | Granger et al. |
| 5,261,914 A | 11/1993 | Warren |
| 5,281,236 A | 1/1994 | Bagnato et al. |
| 5,282,809 A | 2/1994 | Kammerer et al. |
| 5,306,290 A | 4/1994 | Martins et al. |
| 5,320,629 A | 6/1994 | Noda et al. |
| 5,356,413 A | 10/1994 | Martins et al. |
| 5,358,511 A | 10/1994 | Gatturna et al. |
| 5,370,661 A | 12/1994 | Branch |
| 5,370,662 A | 12/1994 | Stone et al. |
| 5,372,146 A | 12/1994 | Branch |
| 5,372,599 A | 12/1994 | Martins |
| 5,380,334 A | 1/1995 | Torrie et al. |
| 5,383,905 A | 1/1995 | Golds et al. |

(List continued on next page.)

FOREIGN PATENT DOCUMENTS

WO 9400079 1/1994

*Primary Examiner*—David O. Reip
*Assistant Examiner*—D Jacob Davis
(74) *Attorney, Agent, or Firm*—Nutter, McClennen & Fish, LLP (57) ABSTRACT

A suture anchor system includes a suture anchor, a first loop of suture thread attached to the suture anchor, a suture needle, and a second loop of suture thread which is attached to the suture needle. The first and second suture loops are interlocked with one another. The suture anchor is preferably bioabsorbable, and it has a flared feature on one side of the second or proximal end thereof. The flared feature renders the suture anchor asymmetrical in a plane that includes the longitudinal axis of the anchor. A method for anchoring soft tissue is also disclosed.

39 Claims, 8 Drawing Sheets

U.S. PATENT DOCUMENTS

| | | |
|---|---|---|
| 5,400,805 A | 3/1995 | Warren |
| 5,405,354 A | 4/1995 | Sarrett |
| 5,417,712 A | 5/1995 | Whittaker et al. |
| 5,500,000 A | 3/1996 | Feagin et al. |
| 5,534,011 A | 7/1996 | Greene, Jr. et al. |
| 5,545,180 A | 8/1996 | Le et al. |
| 5,569,306 A | 10/1996 | Thal |
| 5,578,057 A | 11/1996 | Wenstrom, Jr. |
| 5,584,860 A | 12/1996 | Goble et al. |
| 5,618,314 A | 4/1997 | Harwin et al. |
| 5,782,863 A * | 7/1998 | Bartlett ................ 606/132 |
| 5,782,864 A | 7/1998 | Lizardi |
| 5,814,051 A | 9/1998 | Wenstrom, Jr. |
| 5,873,891 A * | 2/1999 | Sohn .................. 606/219 |
| 5,891,168 A * | 4/1999 | Thal .................. 606/139 |
| 6,156,039 A * | 12/2000 | Thal ................... 606/72 |
| 6,306,158 B1 * | 10/2001 | Bartlett ................ 606/139 |
| 6,355,066 B1 * | 3/2002 | Kim ................... 606/232 |

* cited by examiner

KNOTLESS SUTURE ANCHOR SYSTEM AND METHOD OF USE

CROSS-REFERENCE TO RELATED APPLICATIONS

Not applicable.

STATEMENT REGARDING FEDERALLY SPONSORED RESEARCH

Not Applicable.

FIELD OF THE INVENTION

The invention relates to a knotless suture anchor system for attaching soft tissue to hard bone, and to methods for attaching soft tissue to hard bone.

BACKGROUND OF THE INVENTION

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A number of devices and methods have been developed to attach soft tissue to bone. These include screws, staples, cement, suture anchors, and sutures alone. Some of the more successful methods involve use of a suture anchor to attach a suture to the bone, and tying the suture in a manner that holds the tissue in close proximity to the bone.

The tissue may be attached to the bone during open surgery, or during closed (e.g., arthroscopic) surgical procedures. Closed surgical procedures are preferred since they are less invasive and are less likely to cause patient trauma. In a closed surgical procedure, the surgeon performs diagnostic and therapeutic procedures at the surgical site through small incisions, called portals, using instruments specially designed for this purpose. One problem encountered in the less invasive, closed surgical procedures is that the surgeon has significantly less room to perform the required manipulations at the surgical site. Thus, devices and methods are needed which will allow a surgeon to effectively and easily attach tissue to bone in the small spaces provided by less invasive surgical procedures.

Conventional methods for attaching soft tissue to bone typically require that the surgeon tie a knot in the suture thread to attach the suture to an anchor, or to attach the tissue to the bone using the suture. Knot tying at the surgical site in closed surgical procedures, and even in open surgery, is difficult and time consuming due to inherent space constraints. Further, knots and other bulky attachment means can irritate tissue over time.

Knotless suture anchor systems have been developed for use with closed surgical procedures, and U.S. Pat. No. 5,569,306 provides one example of such a system. A further knotless suture anchor and system is disclosed in U.S. Pat. No. 5,782,864. Although generally useful, such systems can be limited to use only with certain types or shapes of tissue, or to use with certain anatomical structures. Proper attachment of soft tissue requires that it be placed in the anatomically correct position to promote optimal healing.

Further, some conventional knotless suture anchor systems may require, in order to attach a broader array of tissue shapes to bone, that the suture anchor pass though the tissue to be attached. This is undesirable because it unnecessarily irritates the injured tissue and it requires opening a much larger hole in the tissue.

There is thus a need for an improved system for anchoring soft tissue to bone which reduces or eliminates the need to tie suture knots at the surgical site. Further, there is a need for an improved system for anchoring soft tissue to hard bone which is easy and fast to deploy and requires few tools. It would also be advantageous to provide a fully absorbable knotless suture anchor and system.

SUMMARY OF THE INVENTION

The present invention provides a system for anchoring tissue to bone including a suture anchor, a first suture loop attached to the suture anchor, a suture needle and a second suture loop attached to the suture needle and interlocked with the first suture loop. The second suture loop may be formed by attaching two free ends of a length of suture thread directly to the suture needle, or by attaching the two free ends within a suture closure which may then be attached to the suture needle. In a preferred embodiment, the suture anchor is entirely bioabsorbable. A method is also provided by which a detached tissue may be securely attached to bone in an anatomically correct position without the need to tie a knot.

In an exemplary embodiment, the system includes a suture anchor having a first, leading end, a second, trailing end, and two opposed sides between the first and second ends. The second end has a flared portion that renders the suture anchor asymmetrical in a plane that includes the longitudinal axis. The first suture loop is attached at a position between the first and second ends of the suture anchor and is interlocked with the second suture loop. The second suture loop is attached to a trailing end of the suture needle. The asymmetrical shape of the suture anchor assists in securing the anchor within bone. When tension and deflection by the inserter is applied to the suture anchor, after the anchor is positioned within bone, the anchor undergoes a toggling action, or rotation which results in the anchor being oriented in a direction that is not parallel with the longitudinal axis of the anchor-seating bore. This toggling of the anchor causes the anchor to become lodged within the bone. Thus, the anchor can be firmly embedded within bone without the need for ancillary anchoring structure such as arcs.

In an embodiment that is particulary useful in closed surgery, the second suture loop is formed using a suture loop closure and is attached to a hollow suture needle by means of a slot provided in a wall of the hollow needle. This embodiment may also employ an actuator, disposed within the hollow needle, which can be selectively deployed to disengage the second suture loop from the needle. The hollow needle used with this embodiment preferably is part of an elongate tool, such as a suture inserter, that is useful in closed surgical procedures. The hollow needle typically forms the distal end of such a tool.

The system may be used in a method wherein the suture needle and the attached second suture loop are passed through a detached segment of tissue. The second suture loop is pulled through the detached tissue until a portion of the interlocked first suture portion of the first suture loop is seated within a suture thread-engaging groove at the first end of the anchor. The anchor is then tapped into a predrilled bore in a portion of hard bone. Once inside the bone, tension is applied to the anchor by sutures, causing the anchor to toggle such that it is no longer oriented in a direction parallel to the longitudinal axis of the bore, and the flared portion of the anchor engages and is wedged into the wall of the bore. The suture anchor is thus stabilized in an interference fit within the bore, and the detached tissue is thereby attached to the bone in the desired position.

The term "suture needle" is used herein to encompass both conventional suture needles, used in open surgical procedures, as well as suture needles that may form a hollow, distal end of an elongate tool useful with closed surgical procedures.

Further features of the invention, its nature and various advantages, will be more apparent from the accompanying drawings and the following detailed description of the drawings and the preferred embodiments.

BRIEF DESCRIPTION OF THE DRAWINGS

FIG. 8 is a view of the detached tissue with the second suture loop extending there through;

DETAILED DESCRIPTION OF THE INVENTION

Figure 1:
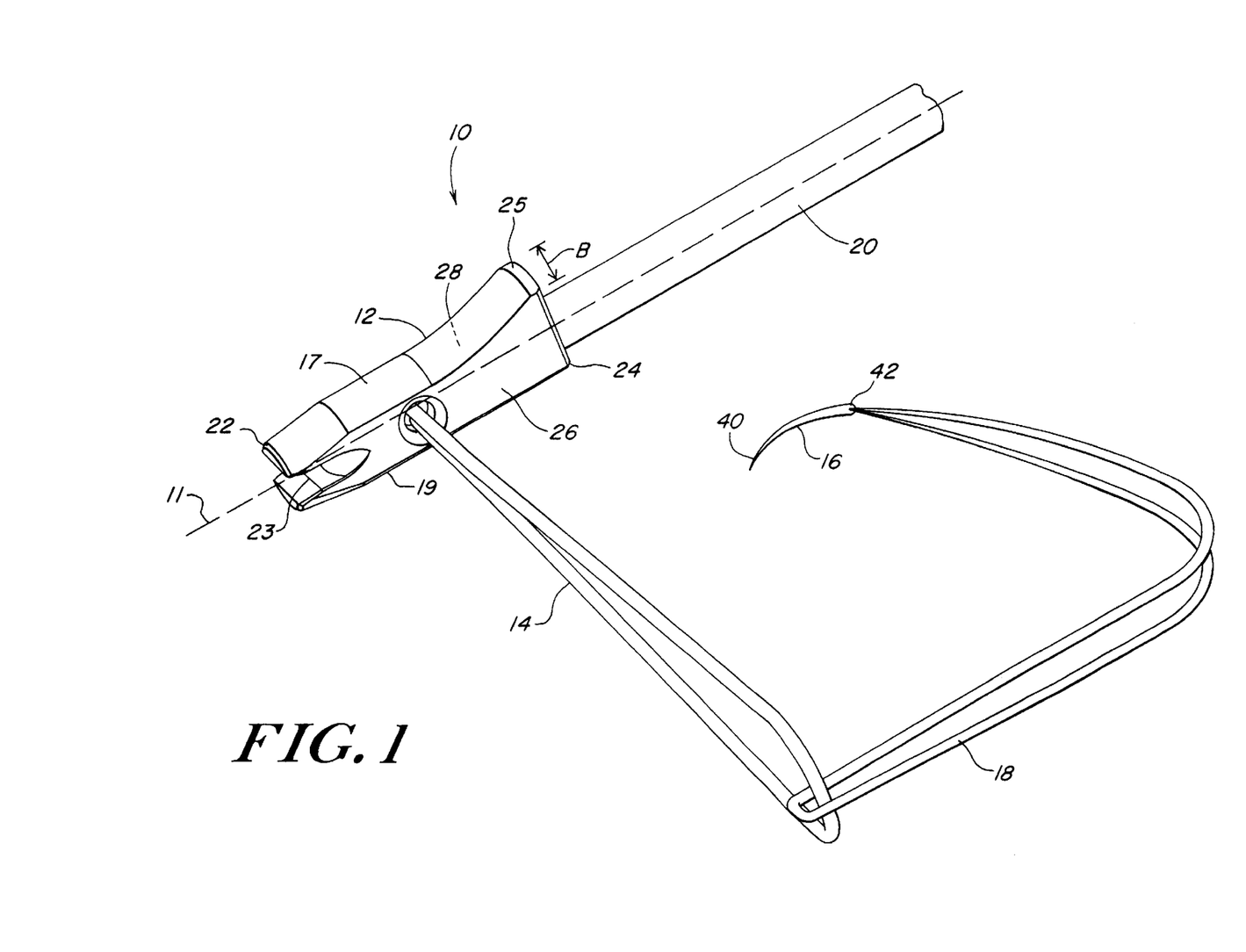
FIG. 1 is a perspective view of an exemplary suture anchor system of the invention.

Referring to FIG. 1, a system 10 for anchoring tissue to bone in accordance with the invention is shown. The system includes a suture anchor 12, a first suture loop 14 attached to the suture anchor 12, a suture needle 16 and a second suture loop 18 attached to the suture needle 16. The first suture loop 14 and the second suture loop 18 are interlocked with each other. The system may also include an anchor inserter tool 20.

The suture anchor 12 has a first, leading end 22 and a second, trailing end 24. The first, leading end 22 tapers, while the second trailing end 24 flares out at one side, rendering the suture anchor asymmetrical in a plane that includes the longitudinal axis 11. In the exemplary embodiment shown in FIG. 1, the suture anchor 12 has two flat, opposed sides 26, 28 between the first and second ends 22, 24 to allow for suture thread to easily pass back and forth. Although sides 26, 28 are shown as flat, it is understood that they may be otherwise shaped or contoured. For example, they may be curved or rounded. The sides 17, 19 adjacent sides 26, 28 may be curved, rounded, or flat.

The exemplary suture anchor 12 additionally comprises a suture thread-engaging groove 23 at the first end 22 for seating portions of the first loop of suture thread 14. The second, trailing end 24 includes a flared portion 25, which is integral with side 17. As shown in FIG. 1, flared portion 25 is located between the two opposed flat sides 26, 28, but it could be located anywhere on the suture anchor. Flared portion 25 may include a sharp edge for penetrating into hard bone, such as cortical bone. Flared portion 25 may also include a knife-like edge (not shown) with a rounded proximal end to promote bone penetration. Additionally, suture anchor 12 may include surface features (not shown) to promote secure seating within bone and to prevent the anchor 12 from backing out of the bone once inserted.

As noted, the flared portion 25 preferably is formed only on one side of the suture anchor 12. The flared portion results from a gradual widening of one side of the anchor. At its maximum dimension, the flared portion causes the suture anchor to be about 0.5 to 1.5 mm, preferably 1.0 mm, wider than it would be without the flared portion. As shown in FIG. 1, the flared portion 25 has a breadth dimension (B) that is consistent with the breadth of side 17, with which it is integral. The breadth (B) of the flared portion 25 is preferably about 0.3 to 1 mm.

The suture anchor 12 may be constructed from suitable metals or polymers known to those of ordinary skill in the art. In a preferred embodiment, suture anchor 12 is fully bioabsorbable and is constructed from a bioabsorbable material such as polylactic acid (PLA) and polysulfone. The suture anchor 12 should have a length sufficient to enable it to properly seat within bone. In an exemplary embodiment, the anchor 12 is about 5 to 15 mm long, with the first, leading end 22 having at its narrowest portion a diameter of about 1 to 3 mm, a middle portion having a diameter of about 2 to 4 mm, and a second, trailing end having at its widest portion a diameter of about 2.5 to 5 mm. In one embodiment, the anchor 12 is about 9 mm long with a leading end diameter of about 2 mm, an intermediate diameter of about 3 mm, and a diameter at the widest portion of the trailing end of about 4 mm. The suture thread-engaging groove 23 can have a depth of about 1 to 2.5 mm and an inner diameter of about 0.5 to 1 mm.

The first suture loop 14 may be suitably attached to the suture anchor 12 through a hole or holes provided in the body of the suture anchor 12 or by a suture retaining slot formed within the body of the suture anchor 12. In the exemplary suture anchor 12, the first suture loop 14 is attached at a location substantially intermediate the first 22 and second ends 24 of the suture anchor 12, and portions of first suture loop 14 extend past the second end 24 on opposed sides 26, 28 of the suture anchor 12.

Figure 3:
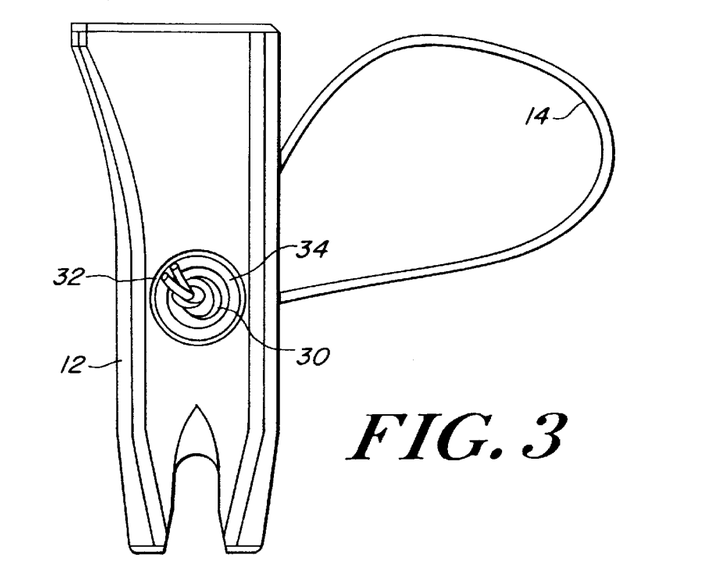
FIG. 3 is a view of the first suture loop engaged with the suture anchor of FIG. 2.

In an additional embodiment, the first suture loop 14 may be attached to the suture anchor 12 as illustrated in FIG. 3. The first suture loop 14 is formed from a length of suture thread by tying the two free ends of the thread into a knot 30. It will be understood that other methods of attaching the two free ends, including the use of suture loop closure devices as further described below with regard to the second suture loop, may be used.

Figure 2:
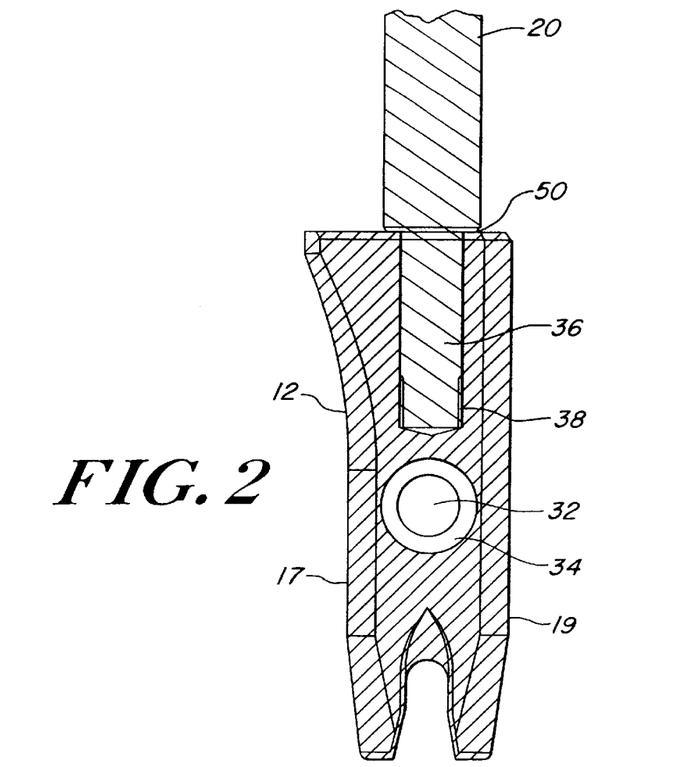
FIG. 2 is a cross-sectional view of a suture anchor attached to an inserter tool.

As shown in FIGS. 2 and 3, the suture anchor 12 includes a through-hole 32 intermediate the first 22 and second ends 24. The through-hole 32 is adapted, by providing varying diameters within the through-hole 32, to retain the first suture loop 14. In an exemplary embodiment, the diameter within the through-hole 32 is varied by providing an annular collar 34 therein. The inner diameter of the annular collar 34 is large enough to allow the unknotted portion of the first suture loop 14 to pass therethrough. The inner diameter of the annular collar 34 is small enough, however, to prevent the knot 30 from passing through the through-hole 32. When the unknotted portion of the first suture loop 14 is drawn through the through-hole 32, as illustrated in FIG. 3, the knot 30 is retained by the annular collar 34 and the first suture loop 14 is thereby attached to the suture anchor 12.

As can further be seen by reference to FIG. 2, the second end 24 of the suture anchor 12 may be provided with a mating feature for mating the suture anchor 12 to the anchor insertion tool 20. As illustrated, anchor insertion tool 20 has a threaded insertion tip 36 that engages a threaded bore 38 formed in the second end 24 of the suture anchor 12. Other configurations may be used as required.

The first suture loop 14 may be constructed from thread suitable for use as a suture. A variety of suture materials are well known to those of ordinary skill in the art. Exemplary materials include braided polyester and polydioxanone (PDS).

The length of the first suture loop 14 may be determined by a person of ordinary skill in the art depending upon the specific application desired for the system. This dimension depends, to a large extent, upon the dimensions of the tissue to be attached, the type of surgery to be performed, and whether an open or closed surgical technique is to be used. By way of example, the length of the first suture loop may range from about one quarter to one and one half inches in procedures to repair a Bankart lesion or a rotator cuff tear. In an exemplary embodiment as used in the method described hereinbelow, the length of the first suture loop 14 is about 0.25 to 2 inches.

Referring again to FIG. 1, the suture needle 16 has a first, tissue penetrating end 40 and a second trailing end 42. The size and shape of the needle used with the system of the invention may be selected by a person of ordinary skill in the art depending upon the specific application of the system, and in particular, depending upon whether the system is used in an open or closed (e.g., arthroscopic) surgical procedure. Generally, needle 16 is at least slightly curved.

In the exemplary embodiment of FIG. 1, which is typically used in open surgical procedures, the second suture loop 18 is attached to the suture needle 16 at the second end 42 of needle 16. One of ordinary skill in the art will appreciate that a number of techniques can be utilized to join the second suture loop 18 to the suture needle 16. For example, the second end 42 of the suture needle 16 can be hollowed so that two free ends of suture thread may be inserted therein. The hollowed end is then crimped to securely retain the two ends of suture thread within the second end 42 of the needle 16, thus creating the second suture loop 18.

Figure 4:
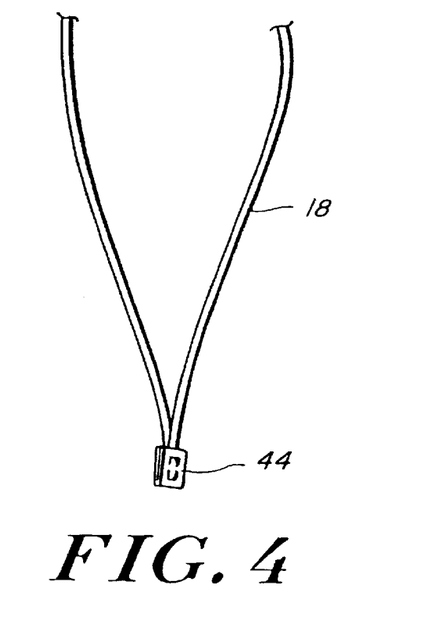
FIG. 4 is a partial view of a second suture loop with a suture loop closure.
Figure 5:
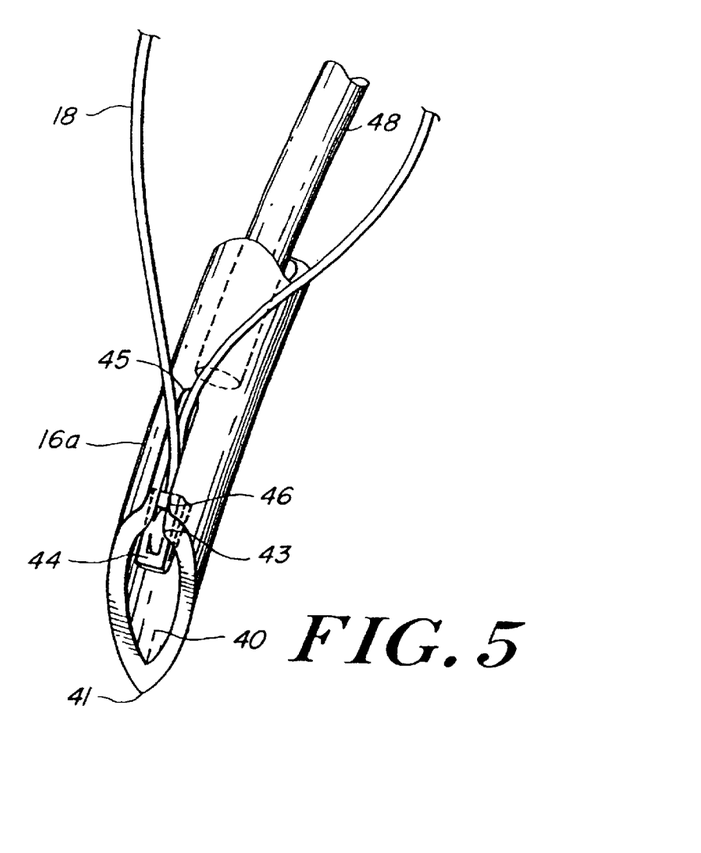
FIG. 5 is a partial view of the second suture loop and suture loop closure of FIG. 4 engaged with a suture needle.

In an alternative embodiment, shown in FIGS. 4 and 5, that is particularly suited for use in closed surgical procedures the second suture loop 18 may be attached to the needle 16a by means of a suture loop closure 44. Referring now to FIG. 4, the second suture loop 18 may be formed by securing two free ends of a length of suture thread within a suture loop closure 44. The suture loop closure 44 may consist of a metal tube having an internal diameter large enough to admit two ends of suture thread. The two free ends of the suture thread are then entered into the suture loop closure 44 and the suture loop closure 44 is crimped to retain the ends of the suture thread and form the second suture loop 18. It will be understood that the suture loop closure 40 may take other forms, including a knot tied with the two free ends of the suture thread.

A second suture loop 18, having a suture loop closure 44, may be attached to a suture needle 16a as shown in FIG. 5. In this exemplary embodiment, the suture needle 16a is a hollow member, having an open distal end 40, one wall of which includes a tissue-penetrating edge or point 41. A slot 46 is formed in the wall of the distal end of the needle, preferably opposite point 41. The slot 46 has an open end 43 that communicates with the open distal end 40 of the suture needle 16a and an opposite, closed end 45. The slot 46 is wide enough to slidably engage the second suture loop 18, but narrow enough to retain the suture loop closure 44 on one side of the slot 46. The second suture loop 18 is then attached to the suture needle 16a by placing the suture loop closure 44 inside the open first end 40 of the hollow suture needle 16a and sliding the suture loop closure 44 and the attached second suture loop 18 within the slot 46 to the closed end thereof.

The hollow suture needle 16a of FIG. 5 may also include an internally disposed actuator 48. The actuator 48 may be a rod that is selectively slidable within the hollow suture needle 16a between a first position, in which the actuator 48 is inside the hollow needle 16a and does not reach the slot 46, and a second position (not shown), in which the actuator 48 extends past the slot 46. Selectively sliding the actuator 48 from the first position to the second position causes the actuator 48 to contact the suture loop closure 44 (and the attached second suture loop 18), causing closure 44 to slide the length of slot 46 and become disengaged from the needle 16.

Suture needle 16a, as noted above, is well suited for use in closed surgical procedures. The suture needle 16a may form the distal end of an elongate suture inserter tool (e.g., an arthroscopic, laparoscopic or endoscopic tool) that is useful in closed surgical procedures.

The second suture loop 18, like the first suture loop 14, may be constructed from well known materials suitable for use as a suture. The length of the second suture loop may be determined by a person of ordinary skill in the art depending upon factors such as the dimensions of the tissue to be attached, the type of surgery to be performed, and whether an open or closed surgical technique is to be used. For example, the length of second loop 18 is generally in the range of about 20 to 40 inches, and more preferably about 30 to 36 inches for closed surgical procedures. Open surgical procedures can utilize a smaller length for second loop 18, in the range of about 6 to 40 inches and more preferably 8 to 10 inches.

It is understood that various anchor insertion tools may be used with the system of the present invention. FIG. 2 illustrates an exemplary insertion tool 20, the distal end 50 of which includes an insertion tip 36 that is threadably mated with the second end 24 of the suture anchor 12. In some embodiments, the suture anchor 12 may be removably premated to the distal end of the insertion tool.

The system of the invention for anchoring tissue to bone may be used in the method described herein below. For purposes of illustration, FIGS. 6–13 depict the method in the context of arthroscopic shoulder repair, more specifically, attaching a detached labrum (as might result from a Bankart lesion or rotator cuff tear) to the glenoid rim of a scapula. It will be understood, however, that the system and method described herein are equally applicable to connecting detached tissue in other contexts as well.

Figure 6:
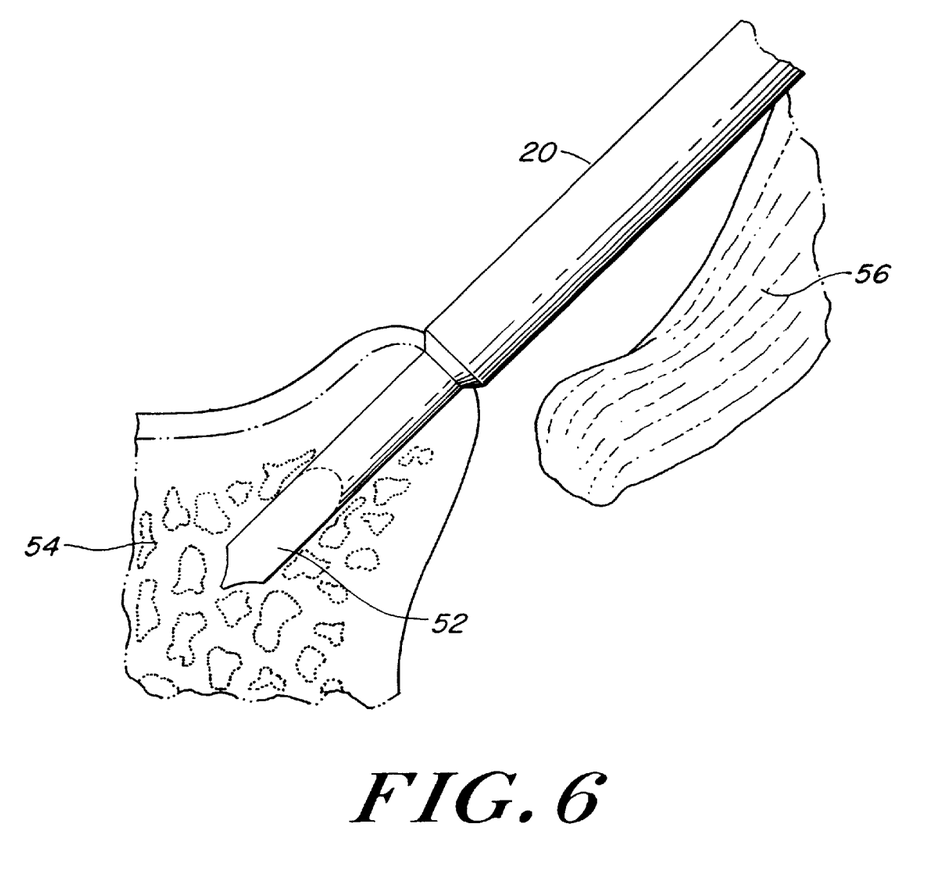
FIG. 6 is a view of a bore being drilled in hard bone for receiving a suture anchor system.

Referring to FIG. 6, a bore 52 is formed in a bone 54. The diameter of the bore 52 should be slightly smaller than the widest portion of the second, trailing end 24 of the suture anchor 12. In an exemplary embodiment, the diameter of the bore 52 is approximately 3 mm when the widest part of the suture anchor is about 4 mm. The length of the bore must be of sufficient length to allow for complete seating of the anchor, and to enable the depth of the anchor to be adjusted to help control the tightness of the first suture loop 14. The actual length of the bore 52 will depend upon the length of the first suture loop 14 and the thickness of the detached tissue 56.

Figure 7:
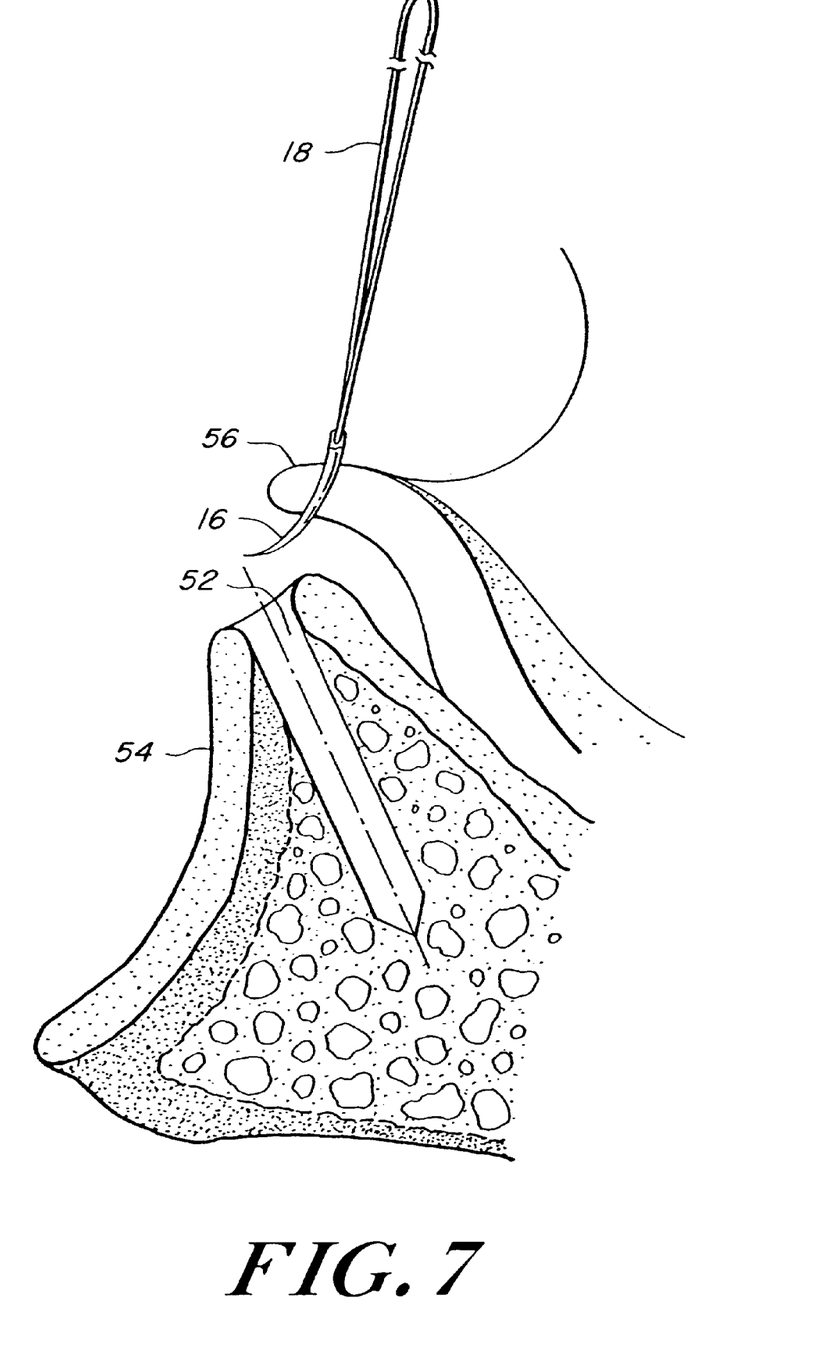
FIG. 7 is a view of a portion of the suture anchor system engaged with a detached tissue.
Figure 8:
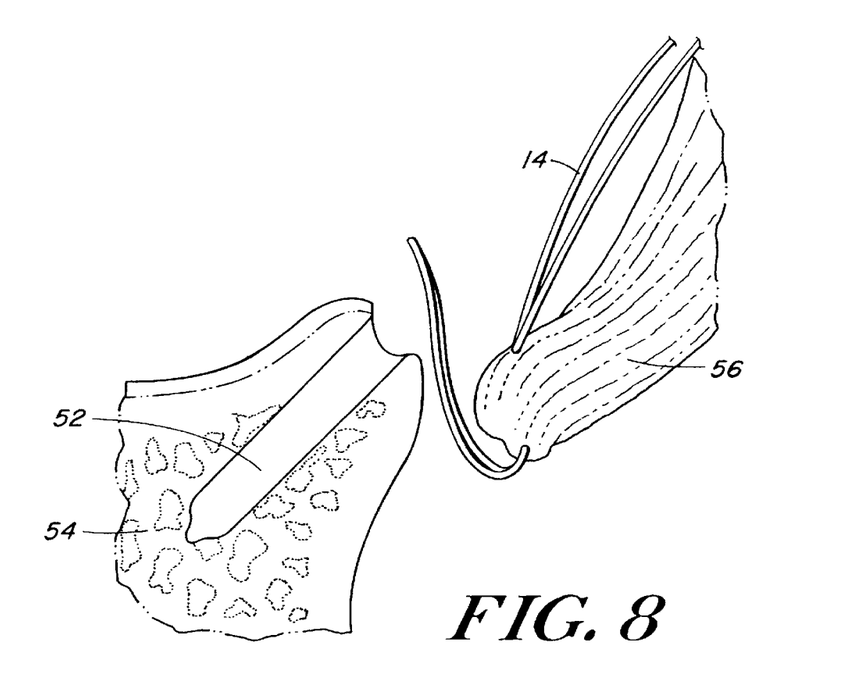

As shown in FIG. 7, the suture needle 16 is then passed through the detached tissue 56. The suture needle 16 and the attached second suture loop 18 are pulled through the detached tissue 56 to advance the interlocked first loop 14 through the tissue, as illustrated in FIG. 8. If the procedure is being performed arthroscopically, the suture needle 16a and the tool with which it is associated will be pulled from, and exit through, an exit portal (not shown).

Alternatively, in embodiments that utilize the needle 16a, shown in FIG. 5, the needle 16a may penetrate the detached tissue 56. The actuator 48 is then selectively moved so as to disengage the suture loop closure 44 and the attached second suture loop 18 from the needle 16a. The suture needle 16a may then be withdrawn from the patient's body from the portal through which the needle entered. A suture grasper or retrograder (not shown) may be used to pull the remaining portion of the second loop 18 through the detached tissue 56.

Figure 9:
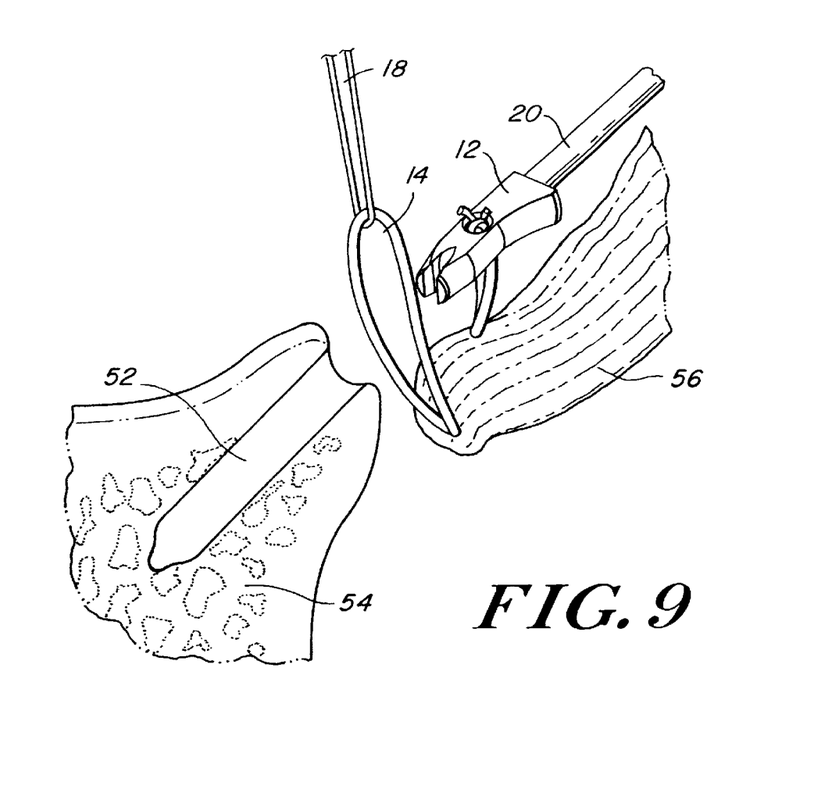
FIG. 9 is a view of a portion of the suture anchor system before the suture anchor is inserted into a bone.
Figure 10:
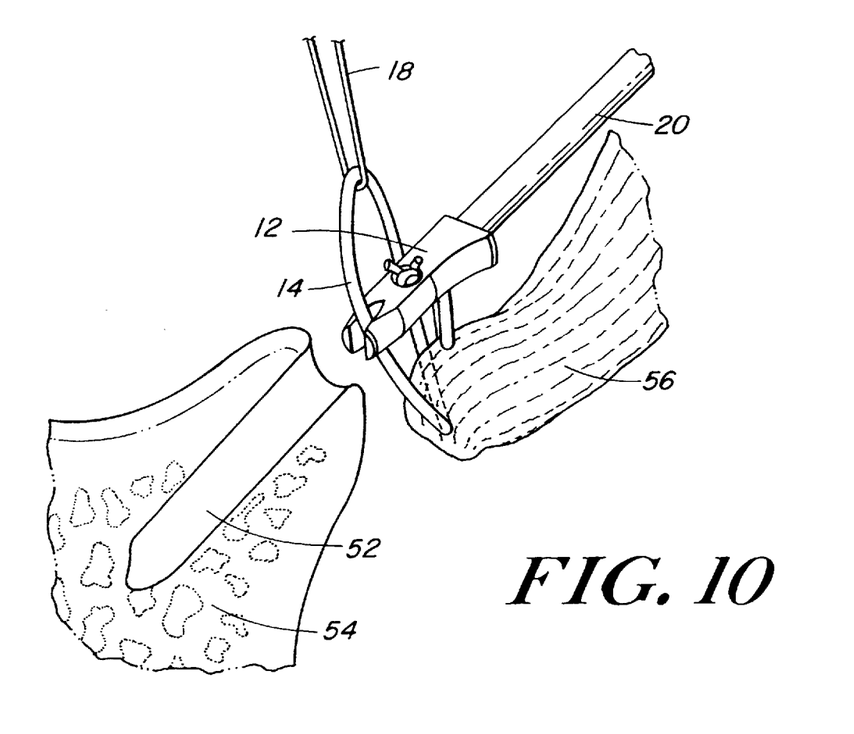
FIG. 10 is a view of a portion of the suture anchor system showing the first suture loop being engaged by the suture anchor.
Figure 11:
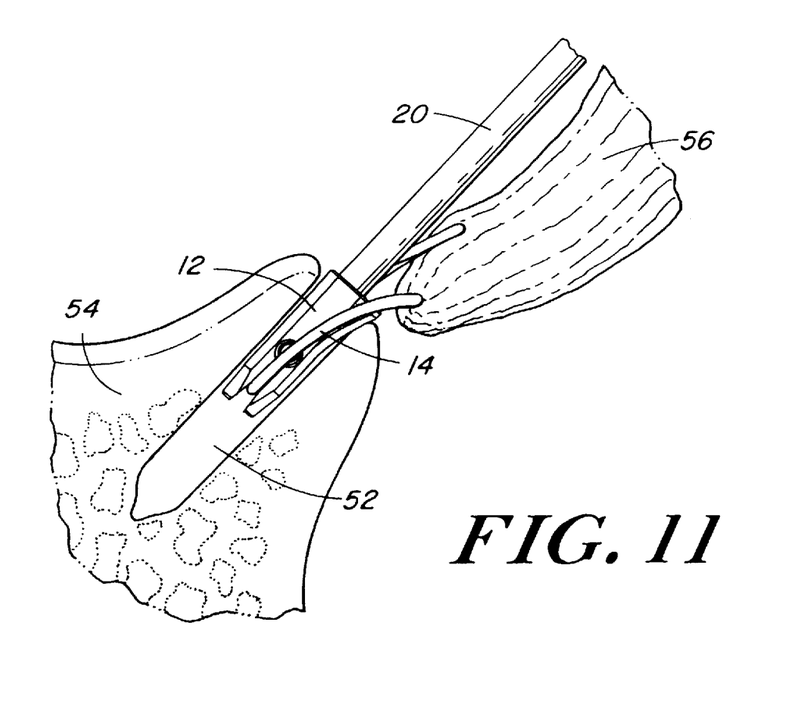
FIG. 11 is a view of a portion of the suture anchor system with the suture anchor partially inserted into a bone.

In FIG. 9, the first suture loop 14 is positioned over the bore 52 by manipulating the position of the second suture loop 18. When the first suture loop 14 is in its desired position, the insertion tool 20 is maneuvered so that a portion of the first suture loop 14 is seated in the suture thread-engaging groove 23 of suture anchor 12, as shown in FIG. 10. Once the first suture loop 14 is seated, the anchor 10 is aligned with the bore 52. By applying force to the insertion tool 20, the suture anchor 12 is forcibly urged into the bore 52. Suture anchor 12 can be tapped into the bore 52, or it can be positioned in another manner. In the case of polymeric suture anchors 12, because the diameter of the bore 52 is slightly smaller than the widest part of the suture anchor 12, some of the polymeric material forming the suture anchor 12 may be scraped off during the insertion step to allow the suture anchor 12 to pass through the opening of the bore 52. When the suture anchor 12 is partially inserted, as illustrated in FIG. 11, the second suture loop 18 can be cut and discarded along with the suture needle 16.

Figure 12:
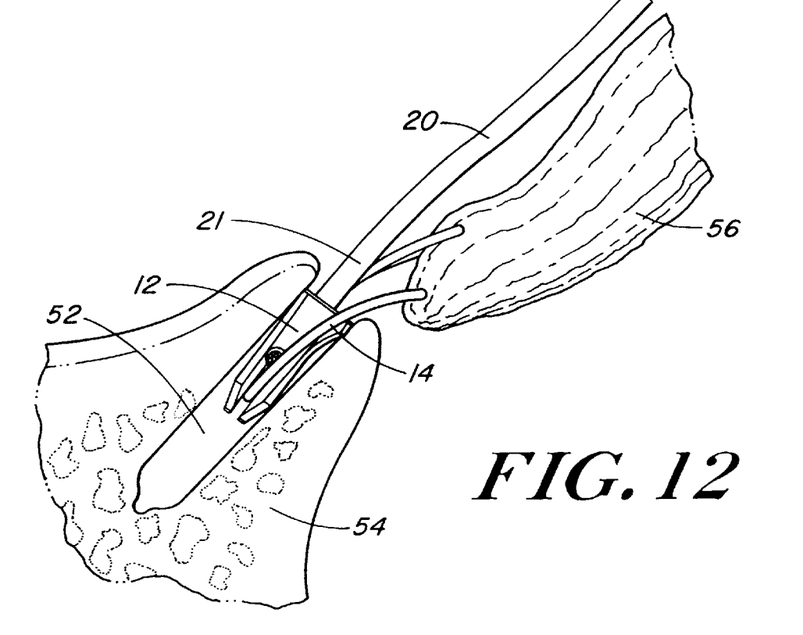
FIG. 12 is a view of a portion of the suture anchor system with the suture anchor fully inserted into a bone.
Figure 13:
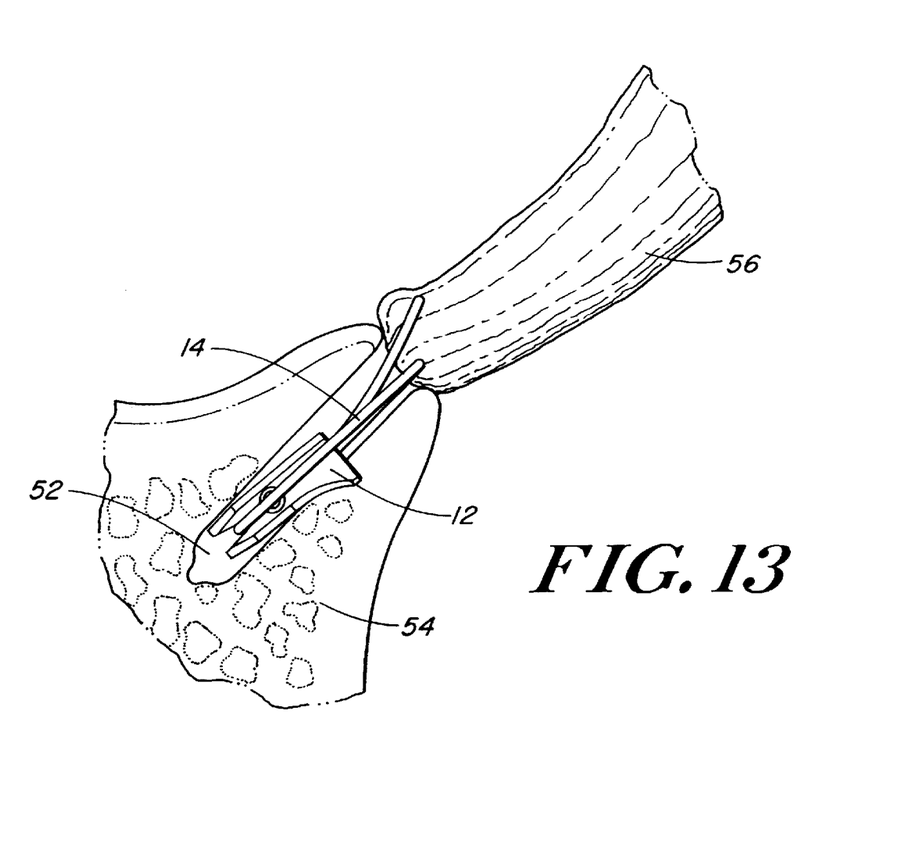
FIG. 13 is a view of a tissue attached to a bone, and a fully seated suture anchor, using the system and method of the invention.

Referring to FIG. 12, when the suture anchor 12 is advanced into the bore 52, there will be a tight interference fit between the bore 52 and the anchor 12. By compressing and manipulating the anchor 12 using the insertion tool 20, the surgeon can wedge the flared portion 25 of the anchor 12 into the bone tissue within the bore 52. Further, when tension is applied to the anchor 12, the asymmetrical shape will cause a toggling of the anchor, resulting in the anchor 12 becoming lodged within the bone 54. As shown in FIG. 12, insertion tool 20 can include a flexible neck, or portion 21 that allows the tool to bend when pressure is exerted. This enables a compressive force to be greater on one side of the anchor, resulting in toggling or rotating the anchor. FIG. 13 shows the suture anchor 12 wedged inside the bore 52, resulting in a snug, anatomically correct attachment of the detached tissue 56 to the bone 54. Once the anchor 10 is inserted into bore 52, the insertion tool 20 may be removed.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A system for anchoring tissue to bone, comprising:
   a suture anchor having a longitudinal axis, a first leading end and a second, trailing end, the first end having formed therein a groove that creates a distal facing opening in the suture anchor and the second end having a flared portion that renders the suture anchor asymmetrical in a plane that includes the longitudinal axis;
   a first loop of suture thread attached to the suture anchor;
   a second loop of suture thread attached to the first loop, wherein the first loop and the second loop are interlocked with one another; and
   a suture needle having a first, tissue penetrating end and a second, trailing end, wherein the suture needle is attached to the second loop.

2. The system of claim 1, wherein the suture anchor includes two substantially flat, opposed sides between the first end and the second end.

3. The system of claim 1, wherein a threaded bore is formed in the suture anchor, extending therein from the second, trailing end.

4. The system of claim 3, further comprising a suture anchor insertion tool, the tool being in the form of an elongate member having a proximal, handle end and a distal end.

5. The system of claim 4, wherein the distal end of the insertion tool includes an externally threaded insertion tip for engaging the threaded bore of the suture anchor.

6. The system of claim 5, wherein the insertion tool further includes a flexible portion that allows the tool to bend.

7. The system of claim 1, wherein the groove is about 1 to 2.5 mm in depth and has an inner diameter of about 0.5 to 1 mm.

8. The system of claim 1, wherein the flared portion has a shape effective to penetrate into hard cortical bone.

9. The system of claim 8, wherein the flared portion is a chamfered flare.

10. The system of claim 8, wherein the flared portion includes a sharp edge.

11. The system of claim 1, wherein the second end is about 2.5 to 5 mm at its widest portion.

12. The system of claim 1, wherein the second loop comprises a suture loop closure and a length of suture thread having two free ends, the two free ends being attached to and secured within the suture loop closure.

13. The system of claim 1, wherein the second loop is attached to the second end of the suture needle.

14. The system of claim 1, wherein the second loop is attached to the suture needle by securing two free ends of suture thread within a hollow formed within the second end thereof.

15. The system of claim 1, wherein the length of the first loop is in the range of about 0.25 to 2 inches.

16. The system of claim 1, wherein the length of the second loop is in the range of about 6 to 40 inches.

17. The system of claim 1, wherein the first loop comprises a length of suture thread having two ends, the two ends being attached to each other by a suture loop closure.

18. The system of claim 1, wherein the suture anchor has a hole, extending transverse to the longitudinal axis, having an inner diameter adapted to allow the first loop to pass through the hole while preventing the suture loop closure from passing through the hole.

19. The system of claim 18, wherein the hole is disposed substantially intermediate the first and second ends of the anchor.

20. The system of claim 1, wherein the suture needle comprises:
- a hollow needle member having an open distal end and a proximal end, the needle member having a substantially cylindrical outer wall;
- a tissue penetrating edge formed at the distal end on one portion of the outer wall; and
- a slot formed on the distal end, on a portion of the outer wall opposite the tissue penetrating edge, the slot having an opening communicating with the open distal end and the slot being adapted to receive and selectively secure the suture loop closure.

21. The system of claim 20, further comprising an actuator member selectively disposed within the needle member, the actuator member being selectively slidable between a first position, wherein the actuator is located entirely within the hollow needle and does not engage the suture needle slot, and a second position, wherein the actuator extends at least to the opening of the slot so as to remove the suture closure from within the slot.

22. The system of claim 21, wherein the actuator member is an elongate rod.

23. The system of claim 20, wherein the needle member is disposed at a distal end of a suture inserter tool.

24. A method for anchoring tissue to bone in a patient's body, comprising the steps of:
- providing a system for anchoring tissue to bone, comprising a suture anchor having a longitudinal axis, a first, leading end and a second, trailing end, the first end having formed therein a groove that creates a distal facing opening in the suture anchor and the second end having a flared portion that renders the suture anchor asymmetrical in a plane that includes the longitudinal axis, a first loop of suture thread attached to the suture anchor, a second loop of suture thread attached to the first loop, wherein the first loop and the second loop are interlocked with one another, and a suture needle having a first, tissue penetrating end and a second, trailing end, wherein the suture needle is attached to the second loop;
- forming a bore in the bone that is accessible through a portal in the patient's body;
- passing the suture needle through a detached segment of tissue;
- pulling the second loop completely through the detached segment of tissue so that a portion of the first loop is positioned over the bore in the bone;
- engaging the first end of the suture anchor with a portion of the suture thread of the first loop;
- inserting the suture anchor at least partially within the bore such that the first suture loop reattaches the detached segment of tissue in a desired position;
- compressing and toggling the suture anchor such that the second end of the anchor penetrates into an inner surface of the bore; and
- anchoring the suture anchor in the bore such that the suture anchor is fixedly attached to the bone.

25. The method of claim 24, wherein the step of engaging the portion of the first loop comprises seating a portion of the suture thread inside the suture thread-engaging groove of the first end of the suture anchor.

26. The method of claim 24, wherein the flared portion is a chamfered flare.

27. The method of claim 26, wherein the flared portion includes a sharp edge.

28. The method of claim 24, wherein the second loop and suture needle are detached after the anchor is inserted into the bore.

29. The method of claim 24, wherein the second loop comprises a suture loop closure and a length of suture thread having two free ends being attached to and secured within the suture loop closure.

30. The method of claim 24, wherein after the suture needle is passed through the detached segment of tissue, an actuator member is employed to disengage the second loop from the slot and the suture needle is withdrawn through the portal.

31. A suture anchor for fixing a suture thread to bone, the suture anchor comprising:
- a substantially elongate body having a longitudinal axis and opposed first and second ends;
- a suture thread-engaging groove formed in the first end to form a distally facing opening in the elongate body; and
- a flared portion, integral with the second end, that renders the suture anchor asymmetrical in a plane that includes the longitudinal axis.

32. The suture anchor of claim 31, wherein the flared portion is effective for penetrating hard cortical bone.

33. The suture anchor of claim 32, wherein the flared portion is a chamfered flare.

34. The suture anchor of claim 32, wherein the flared portion includes a sharp edge.

35. The suture anchor of claim 32, wherein the flared portion includes a knife edge with a flat proximal end.

36. The suture anchor of claim 31, further comprising a threaded bore formed in the second end.

37. The suture anchor of claim 31, further comprising a through-hole substantially intermediate the first and second ends to allow a portion of the suture thread to pass therethrough.

38. The suture anchor of claim 31, wherein the anchor is bioabsorbable.

39. The suture anchor of claim 38, wherein the suture anchor is made of a material selected from the group consisting of polylactic acid and polysulfone.

* * * * *